United States Patent
Inoue et al.

(10) Patent No.: US 10,978,285 B2
(45) Date of Patent: Apr. 13, 2021

(54) ELEMENT ANALYSIS DEVICE AND ELEMENT ANALYSIS METHOD

(71) Applicants: HORIBA, Ltd., Kyoto (JP); HORIBA STEC, Co., Ltd., Kyoto (JP)

(72) Inventors: Takahito Inoue, Kyoto (JP); Hiroshi Uchihara, Kyoto (JP); Kohei Sasai, Kyoto (JP); Toshihiro Ikeyama, Kyoto (JP)

(73) Assignees: HORIBA, LTD., Kyoto (JP); HORIBA STEC, CO., LTD., Kyoto (JP)

( * ) Notice: Subject to any disclaimer, the term of this patent is extended or adjusted under 35 U.S.C. 154(b) by 0 days.

(21) Appl. No.: 16/333,879

(22) PCT Filed: Sep. 22, 2017

(86) PCT No.: PCT/JP2017/034391
§ 371 (c)(1),
(2) Date: Mar. 15, 2019

(87) PCT Pub. No.: WO2018/056419
PCT Pub. Date: Mar. 29, 2018

(65) Prior Publication Data
US 2019/0206667 A1 Jul. 4, 2019

(30) Foreign Application Priority Data

Sep. 23, 2016 (JP) .............................. JP2016-186313
Jun. 1, 2017 (JP) .............................. JP2017-109459

(51) Int. Cl.
*G01N 30/32* (2006.01)
*H01J 49/04* (2006.01)
(Continued)

(52) U.S. Cl.
CPC ............ *H01J 49/049* (2013.01); *G01N 27/62* (2013.01); *G01N 30/32* (2013.01); *G01N 31/12* (2013.01);
(Continued)

(58) Field of Classification Search
CPC ...... H01J 49/049; H01J 49/0027; H01J 49/04; H01J 49/0495; H01J 49/4205; H01J 49/24;
(Continued)

(56) References Cited

U.S. PATENT DOCUMENTS

2004/0247483 A1* 12/2004 Uemura ................. G01N 31/12
422/80
2009/0121129 A1 5/2009 Wang et al.
(Continued)

FOREIGN PATENT DOCUMENTS

CN 101144795 A 3/2008
EP 0964248 A1 12/1999
(Continued)

OTHER PUBLICATIONS

International Search Report dated Dec. 5, 2017 for PCT/JP2017/034391 and English translation.
(Continued)

*Primary Examiner* — Kiet T Nguyen
(74) *Attorney, Agent, or Firm* — Lucas & Mercanti, LLP

(57) ABSTRACT

An objective of this invention is to conduct an accurate quantitative analysis on the Ar element contained in a sample gas by an element analysis device comprising a heating furnace and a mass spectrometer for conducting a quantitative analysis on an element in a vacuum atmosphere. The element analysis device comprises: a heating furnace that heats a graphite crucible containing a sample while introducing a carrier gas into the heating furnace, thereby
(Continued)

vaporizing the sample to generate a sample gas; a quadrupole mass spectrometer that conducts the quantitative analysis on the Ar element contained in the sample gas in a mixed gas comprising the carrier gas and the sample gas discharged from the heating furnace, a first pressure regulator that controls the pressure of the carrier gas to be introduced into the heating furnace, and a second pressure regulator that controls the pressure of the mixed gas discharged from the heating furnace.

11 Claims, 15 Drawing Sheets

(51) Int. Cl.
| | |
|---|---|
| *H01J 49/00* | (2006.01) |
| *H01J 49/42* | (2006.01) |
| *G01N 31/12* | (2006.01) |
| *G01N 27/62* | (2021.01) |
| *H01J 49/24* | (2006.01) |
| *G01N 33/2025* | (2019.01) |
| *G01N 33/00* | (2006.01) |

(52) U.S. Cl.
CPC ..... *G01N 33/0016* (2013.01); *G01N 33/0026* (2013.01); *G01N 33/2025* (2019.01); *H01J 49/0027* (2013.01); *H01J 49/04* (2013.01); *H01J 49/0495* (2013.01); *H01J 49/24* (2013.01); *H01J 49/4205* (2013.01); *G01N 2030/328* (2013.01)

(58) Field of Classification Search
CPC .. G01N 27/62; G01N 30/32; G01N 2030/328; G01N 31/12; G01N 33/2025; G01N 33/0016; G01N 33/0026

USPC ...................................................... 250/288
See application file for complete search history.

(56) References Cited

U.S. PATENT DOCUMENTS

| | | | |
|---|---|---|---|
| 2009/0142619 A1* | 6/2009 | Miyoshi | .................... C23C 4/12 |
| | | | 428/697 |
| 2013/0316465 A1 | 11/2013 | Steude et al. | |
| 2015/0276689 A1* | 10/2015 | Watanabe | ............... G01N 30/32 |
| | | | 422/89 |
| 2019/0027353 A1* | 1/2019 | Hirose | ............... G01N 33/0021 |

FOREIGN PATENT DOCUMENTS

| | | |
|---|---|---|
| JP | S59-083054 A | 5/1984 |
| JP | S60-192258 A | 9/1985 |
| JP | H01183050 A | 7/1989 |
| JP | 2000002699 A | 1/2000 |
| JP | 2009229442 A | 10/2009 |

OTHER PUBLICATIONS

EPO, Extended European Search Report for the European patent application No. 17853187.7, dated Mar. 11, 2020.

Boom R et al., "Argon solubility in liquid steel," Metallurgical and Materials Transactions B, Oct. 1, 2000, pp. 913-919, vol. 31, No. 5, Springer-Verlag, New York.

CNIPA, Office Action issued for the corresponding Chinese Patent Application No. 201780057514.2, dated Nov. 13, 2020, with English translation.

* cited by examiner

ELEMENT ANALYSIS DEVICE AND ELEMENT ANALYSIS METHOD

CROSS REFERENCE TO RELATED APPLICATION

This Application is a 371 of PCT/JP2017/034391 filed on Sep. 22, 2017 which, in turn, claimed the priority of Japanese Patent Application No. 2016-186313 filed on Sep. 23, 2016 and Japanese Patent Application No. 2017-109459 filed on Jun. 1, 2017, all applications are incorporated herein by reference.

FIELD OF THE ART

This disclosure relates to an element analysis device and an element analysis method.

BACKGROUND ART

As shown in the patent document 1, some conventional element analysis device puts a sample into a graphite crucible housed in a heating furnace, produces a sample gas by evaporating the sample by generating Joule heat by flowing impulse current in the graphite crucible while introducing a carrier gas into the heating furnace, introduces a mixed gas comprising the carrier gas and the sample gas discharged from the heating furnace into a quadrupole mass spectrometer (Q-MS), extracts an element contained in the sample gas in the mixed gas and conducts a quantitative analysis on the element.

However, it was not possible for the conventional element analysis device to fully reduce the pressure of the mixed gas discharged from the heating furnace until the mixed gas was introduced into the quadrupole mass spectrometer so that it was difficult for the quadrupole mass spectrometer to conduct the element contained in the sample gas in the mixed gas with high accuracy.

More specifically, the quadrupole mass spectrometer ionizes the sample gas introduced into an ionization part by thermoelectron released from high temperature filament, followed by introducing the ion produced by the ionization part into the quadrupole mass spectrometer, classifies the ion by applying DC and AC to, for example, four columnar electrodes, finally detects the ion that is classified by the quadrupole mass spectrometer by means of an ion detecting part and conducts the quantitative analysis on the element contained in the sample gas by making use of the principle of a property that the element contained in the sample gas changes in accordance with an amount (a partial pressure·a concentration) of the element possessed by the ion current. However, if the atmosphere pressure of the quadrupole mass spectrometer becomes high, probability of collision between the ion flying in the quadrupole mass spectrometer and a gaseous body becomes high so that it becomes difficult for the ion to reach the ion detection part. In addition, since detection sensitivity of the ion detection part changed due to an influence of space charge, if the atmosphere pressure exceeds the maximum working pressure (for example, 1.5 Pa), the ion current begins to decrease. Then the sample gas whose pressure exceeds the maximum working pressure is introduced into the quadrupole mass spectrometer, measurement accuracy is lowered.

However, in accordance with the above-mentioned conventional element analysis device, since the pressure of the mixed gas discharged from the heating furnace is very high and it is not possible to reduce the pressure of the mixed gas sufficiently prior to introducing the mixed gas into the quadrupole mass spectrometer, the measurement accuracy is lowered. Then, it is not possible to satisfy requirement to measure the concentration of Ar contained in metal power if the concentration is low. A new element analysis device that can satisfy this requirement should be developed.

PRIOR ART DOCUMENTS

Patent Document

Patent document 1: Japanese Unexamined Patent Application Publication No. 2000-2699

SUMMARY OF THE DISCLOSURE

It is an object of the present disclosure to provide an element analysis device wherein a heating furnace and a mass spectrometer that conducts a quantitative analysis on an element in a vacuum atmosphere are combined that can conduct a quantitative analysis on the element contained in a sample gas with high accuracy.

Means to Solve the Problems

More specifically, an element analysis device in accordance with an embodiment of this invention comprises a heating furnace that produces a sample gas by heating a crucible that contains a sample while introducing a carrier gas so as to evaporate at least a part of the sample, a mass spectrometer that extracts an element contained in the sample gas in a mixed gas comprising the carrier gas and the sample gas discharged from the heating furnace in a vacuum atmosphere and that conducts a quantitative analysis on the element, a first pressure regulator that controls pressure of the carrier gas to be introduced into the heating furnace, and a second pressure regulator that controls pressure of the mixed gas to be introduced into the mass spectrometer.

In accordance with this arrangement, since high pressure of the carrier gas to be introduced into the heating furnace is reduced by the first pressure regulator, and the pressure of the mixed gas comprising the carrier gas and the sample gas discharged from the heating furnace is reduced by the second pressure regulator so that the pressure is reduced in stages, the pressure of the mixed gas to be introduced into the mass spectrometer is reduced to the pressure suitable for the mass spectrometer so that analysis accuracy is improved. The vacuum atmosphere in this disclosure indicates a state wherein a predetermined vacuum degree is held.

In addition, another arrangement of the element analysis device is the element analysis device that further comprises a vacuum chamber to which the mass spectrometer is connected, and total amount of the mixed gas discharged from the second pressure regulator is introduced into the vacuum chamber.

In addition, further different arrangement of the element analysis device is the element analysis device that further comprises a suction pump that is arranged on a branch line that branches and extends from a position between the second pressure regulator and the mass spectrometer and that sucks the mixed gas discharged from the second pressure regulator.

In accordance with this arrangement, since the mixed gas decompressed by the second pressure regulator easily flows to a side (downstream side) of the mass spectrometer by sucking the mixed gas by the suction pump so that it becomes possible to conduct gas substitution in the side of the mass spectrometer quickly. Further, a part of the mixed gas is exhausted by the suction pump and the remaining mixed gas flows into the mass spectrometer so that time of the mixed gas residing in the discharging line becomes short, it is possible to shorten analysis time by the mass spectrometer. As a result of this, it becomes possible to shorten time necessary for whole of the analysis work. Furthermore, it is possible to further reduce the pressure of the mixed gas by sucking the mixed gas whose pressure is reduced by the second pressure regulator by the use of the suction pump.

In addition, another arrangement of the element analysis device comprises a flow rate adjusting valve arranged in the downstream side of the second pressure regulator. The flow rate adjusting valve is preferably arranged in the upstream side of the branch line. In accordance with this arrangement, since the flow rate of the mixed gas whose pressure is reduced by the second pressure regulator is reduced by the flow rate adjusting valve, it is possible to further reduce the pressure of the mixed gas. In addition, another arrangement of the element analysis device is an element analysis device wherein the mass spectrometer is connected to the vacuum chamber and the vacuum chamber is connected to the suction pump through a flow channel expanding toward the downstream side. In accordance with this arrangement, it is possible to introduce much more mixed gas into the vacuum chamber in the measurement by the mass spectrometer. Accordingly, the S/N ratio is improved.

In addition, another arrangement of the element analysis device may control the pressure of the carrier gas to be introduced into the heating furnace within a range by the first pressure regulator within a range more than or equal to 20 kPa and less than or equal to 80 kPa. If the pressure of the carrier gas to be introduced into the heating furnace is reduced to less than 20 kPa by the first pressure regulator, the gas stagnates inside of the heating furnace at a time of degassing and this will influence on the subsequent measurement. Meanwhile, if the pressure of the carrier gas is reduced only to a pressure exceeding 80 kPa, it is not possible to reduce the pressure of the sample gas enough by the second pressure regulator and the mixed gas stagnates upstream side of the second pressure regulator in the discharging line. Accordingly, the S/N ratio is lowered.

In addition, another arrangement of the element analysis device may be an element analysis device wherein the sample is an Ar containing sample, and the mass spectrometer is a quadrupole mass spectrometer, and comprising an information processing unit that conducts a quantitative analysis on the element contained in the sample gas based on a reference analysis data that indicates a chronological change of current intensity obtained (i) by heating the crucible into which a bath agent containing a main component of the sample is put while introducing the carrier gas into the heating furnace, (ii) by heating the crucible without putting the sample into the crucible and heating the sample while introducing the carrier gas into the heating furnace and (iii) by introducing the carrier gas discharged from the heating furnace into the quadrupole mass spectrometer, and a measurement analysis data that indicates the chronological change of the current intensity obtained (i) by putting the sample into the crucible and heating the crucible while introducing the carrier gas into the heating furnace, (ii) and by introducing the mixed gas comprising the carrier gas and the sample gas discharged from the heating furnace into the quadrupole mass spectrometer.

In accordance with this arrangement, the current intensity of the reference analysis data generally coincides with the current intensity of the measurement analysis data about in a period of time when the peak of Ar appears so that it is possible to conduct the quantitative analysis on the element contained in the sample gas based on the reference analysis data and the measurement analysis data with high accuracy. Degassing may be conducted by heating the crucible into which the bath agent containing Fe is put while introducing the carrier gas into the heating furnace and by discharging the generated gas from the purge line.

In addition, the information processing unit may conduct the quantitative analysis on the element contained in the sample gas based on a difference area between a total reference area and a total measurement area. The total reference area is obtained by drawing straight lines parallel to the current intensity axis from each of plot points of the reference analysis data measured during the predetermined time period while the element contained in the sample gas is detected to a time axis and calculating each of reference part areas of a part locating between two adjacent straight lines, and calculating the total reference area by integrating every reference part area. The total measurement area is obtained by drawing straight lines parallel to the current intensity axis from each of plot points of the measurement analysis data measured during the predetermined time period to the time axis and calculating each of measurement part areas of a part locating between two adjacent straight lines and calculating the total measurement area by integrating every measurement part area. In accordance with this arrangement, the measurement accuracy is improved in case that the time interval between each plot points of the reference analysis data and the time interval between each plot points of the measurement analysis data are not constant, compared with a case that the quantitative analysis is conducted on the element contained in the sample gas based on the difference between the integrated value of the current intensity of each plot point of the reference analysis data and the integrated value of the current intensity of each plot point of the measurement analysis data.

In addition, the element analysis method in accordance with an embodiment of this invention is a method for conducting a quantitative analysis on an element contained in a sample gas produced by evaporating a sample, and is characterized by heating a crucible in a heating furnace into which a bath agent containing a main component of the sample is put while introducing a carrier gas whose pressure is within a range more than or equal to 20 kPa and less than or equal to 80 kPa into the heating furnace, and producing the sample gas by heating the crucible into which an Ar containing sample is put while introducing the carrier gas into the heating furnace, reducing pressure of the mixed gas comprising the carrier gas and the sample gas discharged from the heating furnace to less than or equal to 1.5 Pa and introducing the decompressed mixed gas into a quadrupole mass spectrometer, and extracting the element contained in the sample gas and conducting an quantitative analysis on the element.

Furthermore, in the above-mentioned element analysis method, the quantitative analysis is conducted on the element contained in the sample gas based on a reference analysis data and a measurement analysis data by heating the crucible in the heating furnace into which the bath agent containing the main component of the sample is put while introducing the carrier gas whose pressure is within the range more than or equal to 20 kPa and less than or equal to 80 kPa into the heating furnace, by obtaining the reference analysis data that indicates a chronological change of current intensity by heating the crucible in the heating furnace into which no sample is put while introducing the carrier gas into the heating furnace, by reducing the pressure of the carrier gas discharged from the heating furnace to less than or equal to 1.5 Pa and by introducing the decompressed carrier gas into the quadrupole mass spectrometer, and by obtaining the measurement analysis data that indicates the chronological change of the current intensity by producing the sample gas by heating the crucible in the heating furnace into which the Ar containing sample is put while introducing the carrier gas into the heating furnace, by reducing the pressure of the mixed gas comprising the carrier gas and the sample gas discharged from the heating furnace to less than or equal to 1.5 Pa and by introducing the decompressed mixed gas into the quadrupole mass spectrometer.

Effect

In accordance with the arrangement of embodiments of this invention, it is possible for an element analysis device wherein a heating furnace and a mass spectrometer such as a quadrupole mass spectrometer that conducts a quantitative analysis on an element in a vacuum atmosphere are combined to conduct the quantitative analysis on the element contained in a sample gas with high accuracy.

DESCRIPTION OF THE REFERENCE NUMERALS

Figure 1:
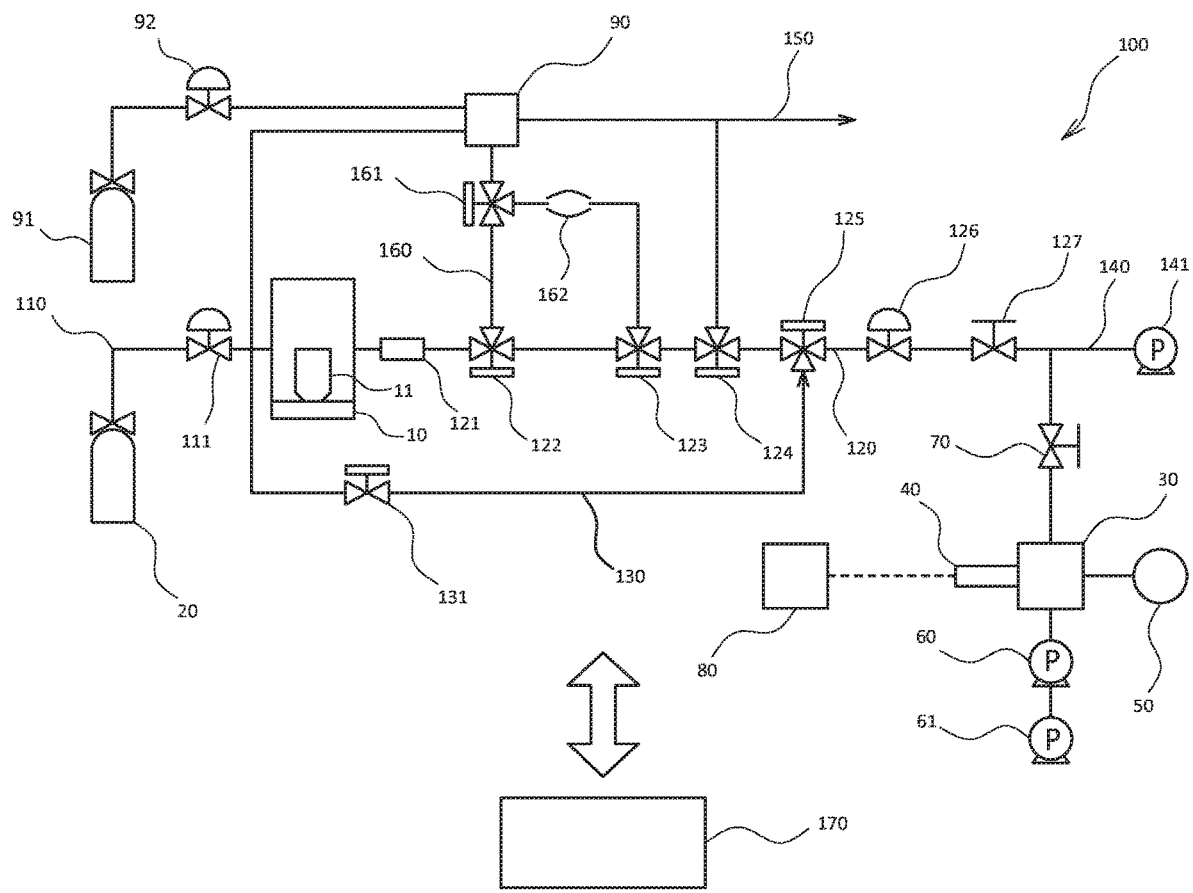
FIG. 1 is a pattern diagram showing an element analysis device in accordance with one embodiment of this invention.

100 . . . element analysis device
10 . . . impulse furnace
11 . . . graphite crucible
20 . . . carrier gas supplier
40 . . . quadrupole mass spectrometer
111 . . . first pressure regulator
126 . . . second pressure regulator
127 . . . flow rate adjusting valve
141 . . . suction pump

MODE FOR EMBODYING THE INVENTION

An element analysis device in accordance with an embodiment of this invention will be explained with reference to drawings.

The element analysis device 100 of this embodiment heats and melts a metal sample (hereinafter also called just as "a sample") that is put into a graphite crucible and that comprises a metal such as titanium, iron, tin or tungsten, or an iron ore or an alloy such as a super alloy, and conducts a quantitative analysis by extracting an element contained in a sample gas that occurs in case of heating and melting the metal sample. In this embodiment, an iron ore that contains Ar and whose main component is Fe is used as the sample.

The element analysis device 100 comprises, as shown in FIG. 1, an impulse furnace 10, a carrier gas supplier 20 connected to a starting end of an introducing line 110 extending toward an upper stream side from the impulse furnace 10 and a quadrupole mass spectrometer 40 that is mounted on a vacuum chamber 30 connected to a terminal end of a discharging line 120 extending to a downstream side from the impulse furnace 10.

The impulse furnace 10 houses a graphite crucible 11 that puts the sample into the impulse furnace 10. Joule heat is generated by applying impulse electric currents to the graphite crucible 11 so as to produce the sample gas by evaporating at least a part of the sample put into the graphite crucible 11.

Figure 2:
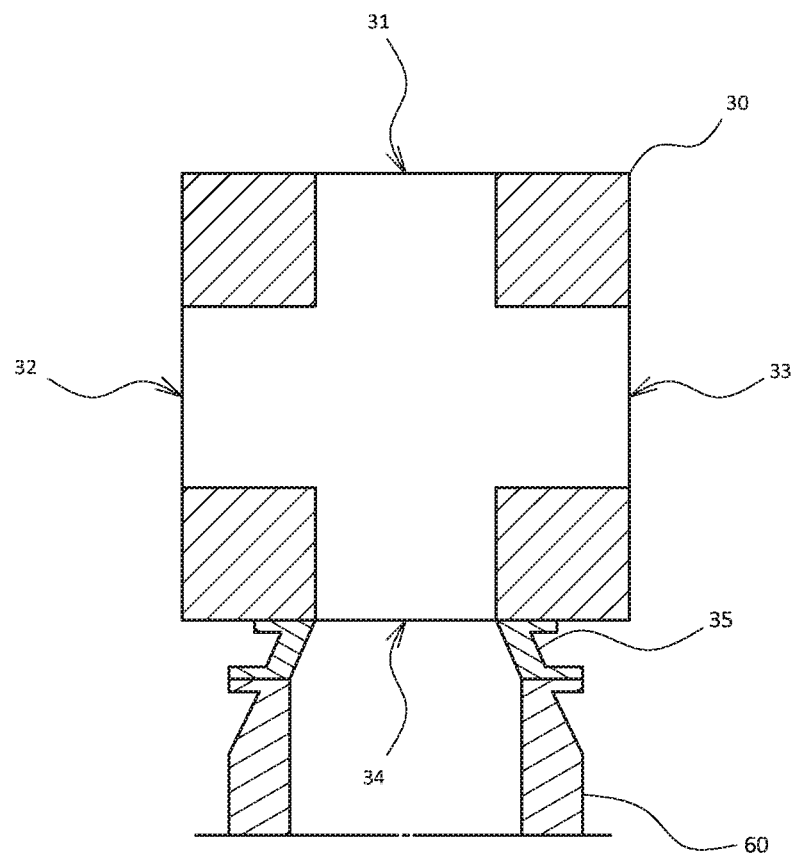
FIG. 2 is a partial cross-sectional view schematically showing a connecting portion between a vacuum chamber and a suction pump in accordance with this embodiment.

The vacuum chamber 30 has a structure comprising connection ports 31, 32, 33, 34 at four sides thereof, and comprises, concretely as shown in FIG. 2, the connection port 31 to which the terminal end of the discharging line 120 is connected, the connection port 32 to which the quadrupole mass spectrometer 40 is connected, the connection port 33 to which a pressure sensor 50 measuring pressure in the vacuum chamber 30 is connected and the connection port 34 to which a turbo suction pump 60 that reduces the pressure in the vacuum chamber 30 is connected. The connection port 34 of the vacuum chamber 30 is connected to the turbo suction pump 60 through a connection pipe 35 having a flow channel tapered extending toward a direction (a downstream side) of the turbo suction pump 60, and no step is formed at junctions between each of the vacuum chamber 30, the connection pipe 35 and the turbo suction pump 60 in the flow channel formed by connecting the vacuum chamber 30, the connection pipe 35 and the turbo suction pump 60. The connection pipe 35 is relatively short. According to these configurations, since the mixed gas introduced into the vacuum chamber 30 from the discharging line 120 is smoothly discharged into the turbo suction pump 60 from the vacuum chamber 30, it is possible to produce an ability of the turbo suction pump 60 to the maxim during a measurement by the quadrupole mass spectrometer 40. Accordingly, it is possible to increase the flow rate of the mixed gas discharged from a flow rate adjusting valve 127, and to increase the flow rate of the mixed gas introduced into the vacuum chamber 30 according to this, resulting in improvement of an S/N ratio.

A dry pump 61 is serially connected in the downstream side of the turbo suction pump 60, and the turbo suction pump 60 and the dry pump 61 are so configured that a rotation number of the pumps 60, 61 can be controlled so as to change the suction flow rate thereof. In addition, a leak valve 70 is arranged on just an upstream side of the terminal end of the discharging line 120, and the leak valve 70 accurately controls a leakage amount of the gas flowing in the discharging line 120 so that the controlled amount of the gas flows in the vacuum chamber 30. A needle valve that adjusts an opening of the valve by changing a distance between a valve sheet and a valve stem may be used as the leak valve 70. In this case, the needle valve is connected to a pipe constituting the discharging line 120 through a connecting pipe in an "in" side that extends toward an upstream side from the valve sheet and a connecting pipe in an "out" side that extends toward a downstream side from the valve sheet Meanwhile, the needle valve for a pipe in a vacuum area (the vacuum chamber 30) is generally the needle valve (a former needle valve) wherein an internal diameter of the connection pipe is relatively big and an internal volume of the connection pipe is relatively big. However, if the needle valve is changed to the needle valve (a later needle valve) wherein an internal diameter of the connection pipe is relatively small and an internal volume of the connection pipe is relatively small, it becomes clear that the following effect can be obtained. More specifically, the following effect can be obtained. In case of using the former needle valve, a peak of a measurement signal of the quadrupole mass spectrometer 40 changes to a broad shape so that a measurement accuracy is lowered. In case of using the later needle valve, the peak of the measurement signal becomes keen so that the measurement accuracy becomes high. Incidentally, the internal volume of the former needle valve is about 10 ml. If the internal volume of the later needle valve is less than or equal to 1 ml, the effect can be remarkable.

Figure 3:
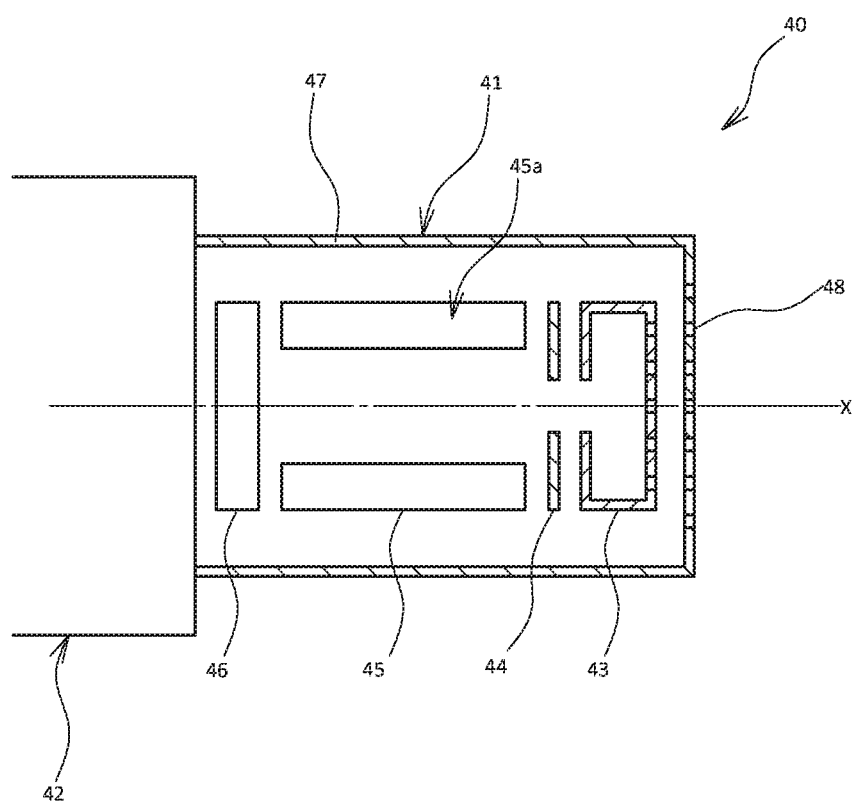
FIG. 3 is a partial cross-sectional view schematically showing a quadrupole mass spectrometer in accordance with this embodiment.

As shown in FIG. 3, the quadrupole mass spectrometer 40 comprises a sensor part 41 that is inserted into the connection port 31 of the vacuum chamber 30 and an information processing unit 42 that is connected to the sensor part 41 and that produces a function as an AC generator. The sensor part 41 comprises an ionization part 43 that ionizes the sample gas, an ion extraction electrode 44 that extracts ions from the ionization part 43, a quadrupole part 45 that selectively passes the ion discharged from the ionization part 43 by the ion extraction electrode 44 and an ion detector 46 that detects the ion passing the quadrupole part 45. The ionization part 43, the ion extraction electrode 44, the quadrupole part 45 and the ion detector 46 are housed in a protection cover 47 in this order from a distal end side, and the ionization part 43, the ion extraction electrode 44, the quadrupole part 45 and the ion detector 46 are arranged on a straight line in the protection cover 47. Concretely, the quadrupole part 45 comprises four rods 45a and a central axis (X) of an inscribed circle of each of the four rods 45a is arranged on the straight line. In case that the protection cover 47 is mounted on the connection port of the vacuum chamber 30, a gas introducing port 48 to introduce the sample gas in the vacuum chamber 30 into inside of the protection cover 47 is formed on a distal end wall of the protection cover 47. The protection cover 47 is airtightly mounted on the connection port of the vacuum chamber 30 through a seal member or the like. According to this arrangement, since the pressure in the protection cover 47 becomes the same as an atmosphere pressure in the vacuum chamber 30 through the gas introducing port 48, the ionization part 43, the ion extraction electrode 44, the quadrupole part 45 and the ion detector 46 are exposed to the atmosphere pressure in the vacuum chamber 30.

A current intensity obtained by the sensor part 41, concretely the ion detector 46 is output to the information processing unit 42. The information processing unit 42 that obtains the current intensity calculates a concentration of the element contained in the sample gas based on the current intensity and outputs the concentration to an output part 80 (a monitor). A concrete configuration of the information processing unit 42 is a general or dedicated computer comprising, for example, a CPU, an internal memory, an input/output interface and an AD convertor or the like, and produces a function to calculate the concentration of the element contained in the sample gas by operating the CPU and its peripheral devices based on programs stored in a predetermined area of the internal memory.

Next, other configuration mounted on the introducing line 110 and the discharging line 120 will be explained.

A first pressure regulator 111 that controls pressure of a carrier gas supplied from a carrier gas supplier 20 to the impulse furnace 10 is arranged on the introducing line 110. The pressure of the carrier gas smaller than or equal to 0.35 MPa supplied from the carrier gas supplier 20 is reduced to a range between 20 kPa and 80 kPa by the first pressure regulator 111. An inactive gas such as helium may be used as the carrier gas.

A dust filter 121, a first three-way valve 122, a second three-way valve 123, a third three-way valve 124, a forth three-way valve 125, a second pressure regulator 126, a flow rate adjusting valve 127 and the leak valve 70 are arranged in this order from the impulse furnace 10 toward the vacuum chamber 30 on the discharging line 120. A furnace evading line 130 extends from a downstream side of the first pressure regulator 111 of the introducing line 120 so as to evade the impulse furnace 10, and a terminal end of the furnace evading line 130 is connected to the discharging line 120 through the forth three-way valve 125. Then, the furnace evading line 130 is selectively switchable to connect with or to disconnect from the discharging line 120 by adjusting the forth three-way valve 125. A two-way valve 131 is arranged in the middle of the furnace evading line 130 and the carrier gas can be drawn from the introducing line 110 to the furnace evading line 130 by opening the two-way valve 131. In addition, a branch line 140 extends from the discharging line 120 locating between the flow rate adjusting valve 127 and the leak valve 70, and a suction pump 141 is arranged at a terminal end of the branch line 141. The suction pump 141 is a dry pump, and can change a suction flow rate by controlling a rotation number of the suction pump 141. Furthermore, a purge line 150 to discharge the gas flowing in the discharging line 120 is connected to the discharging line 120 through the third three-way valve 124, and the purge line 150 is selectively switchable to connect with or to disconnect from the discharging line 120 by adjusting the third three-way valve 124.

The dust filter 121 is to remove foreign substances from the sample gas discharged together with the carrier gas from the impulse furnace 10.

In addition, a buffer line 160 is connected to the discharging line 120 to provide a calibration gas from a gas dozer 90 that produces the calibration gas used for calibrating the element analysis device 100 to the discharging line 120. A starting end of the buffer line 160 is connected to the gas dozer 90 and the buffer line 160 is bifurcated through a fifth three-way valve 161 and one of the terminal ends is connected to the first three-way valve 122 and the other terminal end is connected to the second three-way valve 123. Then, the buffer line 160 is selectively switchable to connect with or to disconnect from the discharging line 120 by adjusting the first three-way valve 122 and the second three-way valve 123. A buffer pipe 162 is arranged between the fifth three-way valve 161 and the second three-way valve 123.

The gas dozer 90 mixes the carrier gas supplied from the carrier gas supplier 20 through the first pressure regulator 111 and an element gas (Ar gas in this embodiment) supplied from an element gas supplier 91 through a third pressure regulator 92, and produces the calibration gas containing a predetermined amount (concentration) of the element (Ar) as being an object to be measured. The gas dozer 90 is connected to the purge line 150 so that the unnecessary calibration gas can be discharged through the purge line 150.

The buffer pipe 162 has a shape whose center part is thicker than both ends that are connected to the buffer line 160. An internal diameter of the thick center part of the buffer pipe 162 is bigger than the internal diameter of the buffer line 160. According to this arrangement, the flow rate of the sample gas discharged from the impulse furnace 10 becomes generally the same as the flow rate of the element gas discharged from the buffer pipe 162. If the element contained in the calibration gas passing the buffer pipe 124 is measured by the quadrupole mass spectrometer 40, it is possible to obtain almost the same peak waveform as the peak waveform at a time when the element contained in the sample gas discharged from the impulse furnace 10 is measured by the quadrupole mass spectrometer 40.

The second pressure regulator 126 controls the pressure of the mixed gas comprising the carrier gas discharged from the impulse furnace 10 and the sample gas. The second pressure regulator 126 reduces the pressure of the mixed gas whose pressure discharged from the impulse surface 100 is between 20 kPa and 80 kPa.

The flow rate adjusting valve 127 controls the flow rate of the mixed gas flowing in the discharging line 120. The flow rate adjusting valve 127 can reduce the pressure of the mixed gas by limiting the flow rate of the mixed gas.

Concretely, for example, the pressure of the mixed gas comprising the carrier gas and the sample gas discharged from the impulse furnace 10 is reduced by the second pressure regulator 126, next the flow rate of the mixed gas is limited by the flow rate adjusting valve 127, and then the mixed gas is sucked by the suction pump 141 so that the pressure of the mixed gas is reduced in stages until it becomes 1.5 Pa or less.

Each component such as the impulse furnace 10, the carrier gas supplier 20, the quadrupole mass spectrometer 40, the suction pumps 60, 61, the leak valve 70, the first pressure regulator 111, the first three-way valve 122, the second three-way valve 123, the third three-way valve 124, the forth three-way valve 125, the second pressure regulator 126, the flow rate adjusting valve 127, the two-way valve 131, the suction pump 141, the gas dozer 90, the element gas supplier 91, the third pressure regulator 92, the fifth three-way valve 161 that constitutes the element analysis device 100 is connected to a control unit 170, and the control unit 170 controls operation of each component during a process of calibration or a process of analysis to be described later. A concrete configuration of the control unit 170 is a general or dedicated computer comprising, for example, a CPU, an internal memory, an input/output interface and an AD convertor or the like, and produces a function to control the operation of each component by operating the CPU and its peripheral devices based on programs stored in a predetermined area of the internal memory or an instruction input from the input/output interface by an operator.

Next, an operation in case of measuring the concentration of Ar contained in the sample by the use of the element analysis device 100 will be explained.

Figure 4:
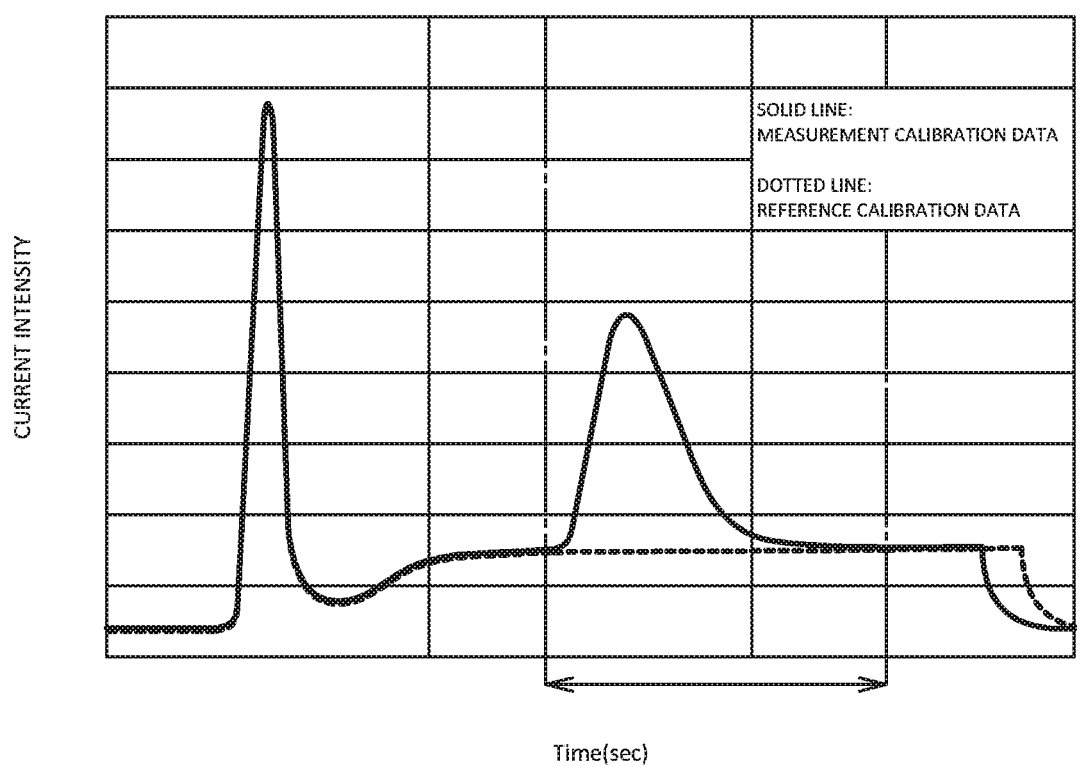
FIG. 4 is a graph showing a reference calibration data and a measurement calibration data obtained by a calibration operation of the element analysis device in accordance with this embodiment.

First, an operation of calibrating the element analysis device 100 is conducted. The operation of calibration comprises the following two processes. First, the control unit 170 sets the element analysis device 100 in a first state wherein the furnace evading line 130 is cut from the discharging line 120 by adjusting the forth three-way valve 125, the buffer line 160 is cut from the discharging line 120 by adjusting the first three-way valve 122 and the second three-way valve 123, and the purge line 150 is cut from the discharging line 120 by adjusting the third three-way valve 124, starts an analysis by the quadrupole mass spectrometer 40 while supplying the carrier gas to the impulse furnace 10 from the carrier gas supplier 20 in this first state without applying electric currents to the graphite crucible 11 of the impulse furnace 10, and obtains a reference calibration data (data shown by dotted lines in FIG. 4) indicating a chronological change of the current intensity obtained from the carrier gas discharged from the impulse furnace 10 in a state wherein no current is applied to the graphite crucible 11. Next, the control unit 170 sets the element analysis device 100 in a second state wherein the furnace evading line 130 is connected to the discharging line 120 by adjusting the forth three-way valve 125 in the first state, and the buffer line 160 is connected to the discharging line 120 by adjusting the first three-way valve 122 and the second three-way valve 123, introduces the carrier gas into the discharging line 120 through the two-way valve 131 and the calibration gas into the discharging line 120 from the gas dozer 90 through the fifth three-way valve 161 in this second state, and then starts an analysis by the quadrupole mass spectrometer 40 and obtains a measurement calibration data (data shown by solid lines in FIG. 4) indicating the chronological change of the current intensity obtained from the calibration gas.

Figure 5:
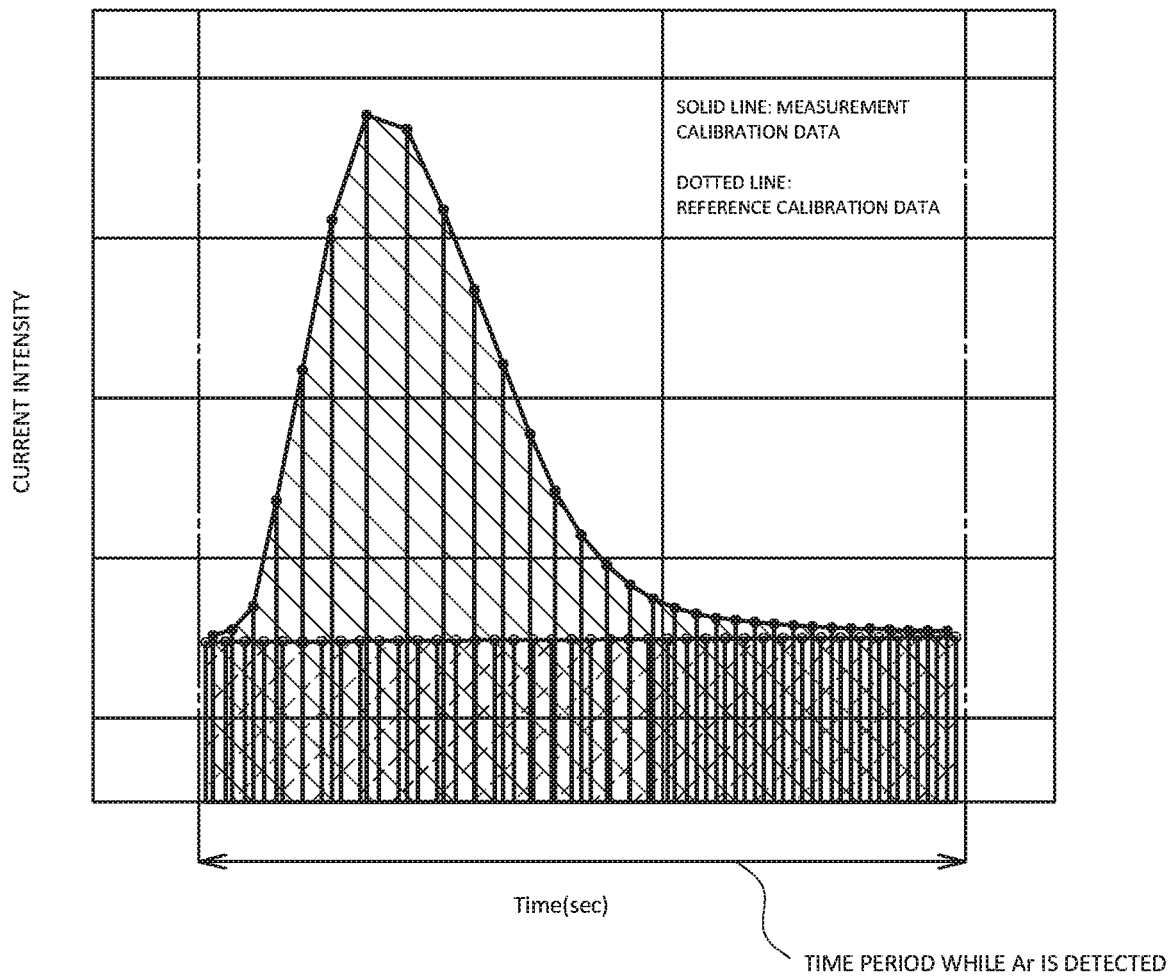
FIG. 5 is a graph to explain a method for calculating a concentration of Ar based on the reference calibration data and the measurement calibration data obtained by the calibration operation of the element analysis device in accordance with this embodiment.

The information processing unit 42 of the quadrupole mass spectrometer 40 calculates the concentration of Ar contained in the calibration gas based on the reference calibration data and the measurement calibration data, and judges whether or not the calculated concentration coincides with an already-known concentration of Ar contained in the calibration gas. Concretely, as shown in FIG. 5, first, specify a detection time period (a time period shown by an arrow in FIG. 4 and FIG. 5) while Ar is detected. Next, concerning the reference calibration data, draw straight lines parallel to a current intensity axis from each of plot points (points shown by white circles in FIG. 5) measured during the detection time period to a time axis and calculate each of reference part areas of a part surrounded by adjacent straight lines (more specifically, a rectangular part surrounded by four straight lines; each of the adjacent straight lines, a straight line connecting adjacent plot points locating at one end of the adjacent straight lines and a straight line connecting adjacent intersections of the time axis and the other end of each of the adjacent straight lines), and calculate a reference total area by integrating every reference part area (an area of a part shown by broken line hatchings in FIG. 5). Similarly, concerning the measurement calibration data, draw straight lines parallel to the current intensity axis from each of plot points (points shown by black circles in FIG. 5) measured during the detection time period to the time axis and calculate each of measurement part areas of a part surrounded by adjacent straight lines (more specifically, a trapezoid part surrounded by four straight lines; each of the adjacent straight lines, a straight line connecting adjacent plot points locating at one end of the adjacent straight lines and a straight line connecting adjacent intersections of the time axis and the other end of each of the adjacent straight lines), and calculate a measurement total area by integrating every measurement part area (an area of a part shown by solid line hatchings in FIG. 5). Finally, calculate a difference area between the measurement total area and the reference total area, and calculate the concentration of Ar contained in the measurement calibration gas based on the difference area. Since gain in accordance with detection used by the quadrupole mass spectrometer 40 is changed according to the current intensity, it takes time to switch the gain so that there is a difference between the time interval of the plot point of the reference calibration data and the time interval of the plot point of the measurement calibration data. In addition, during the later process, since Ar is detected comparatively for a long period of time because the calibration gas is gradually introduced to the discharging line 120 through the buffer pipe 124 without forming a sharp peak waveform indicating Ar in the measurement calibration data, it is possible to calculate the concentration of Ar contained in the calibration gas with high accuracy. In addition, during the later process, since the carrier gas is introduced into the discharging line 120 through the furnace evading line 130, it is possible to prevent an extreme decline of the pressure in the discharging line 120 during the later process. As a result of this, the mixed gas discharged from the impulse furnace 10 smoothly flows to the downstream side of the discharging line 120 during an analysis operation conducted in succession so that it is possible to prevent time loss in the analysis operation.

Subsequently, the analysis operation is conducted on the sample containing Ar by the use of the element analysis device 100 on which the calibration operation has been conducted, however, in order to improve the measurement accuracy to conduct the analysis, we faced a problem when the experiment was repeatedly conducted while adjusting each component constituting the element analysis device 100.

Figure 6:
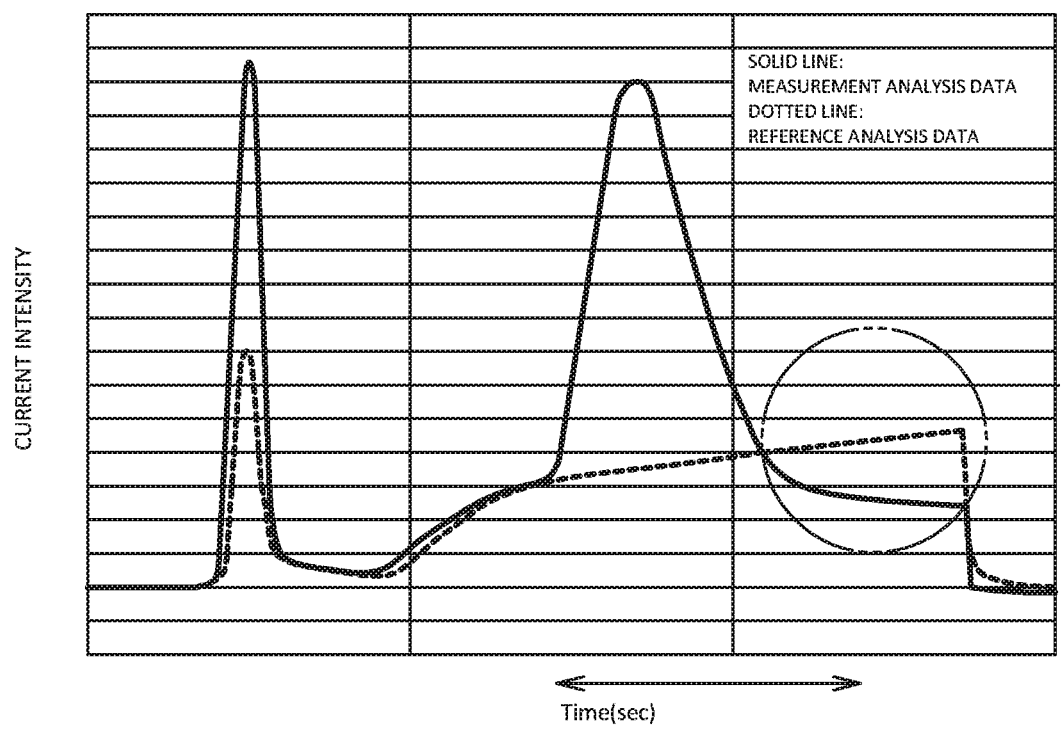
FIG. 6 is a graph showing the reference analysis data and the measurement analysis data obtained by an ordinary analysis operation of the element analysis device in accordance with this embodiment.

More specifically, first, the control unit 170 sets the element analysis device 100 in a third state wherein the furnace evading line 130 is cut from the discharging line 120 by adjusting the forth three-way valve 125, the buffer line 160 is cut from the discharging line 120 by adjusting the first three-way valve 122 and the second three-way valve 123, and the purge line 150 is connected to the discharging line 120 by adjusting the third three-way valve 124, conducts degassing in the third state by applying the electric currents to the graphite crucible 11 in a state that no sample is put into the graphite crucible 11 while supplying the carrier gas to the impulse furnace 10 from the carrier gas supplier 20, switches the third state to the forth state (the same state as the first state) wherein the purge line 150 is cut from the discharging line 120 by adjusting the third three-way valve 124 with keeping the state wherein electric currents are applied, initiates the analysis by the quadrupole mass spectrometer 40 at a time when a predetermined time passes, and obtains a reference analysis data (data shown by a dotted line in FIG. 6) indicating a chronological change of the current intensity obtained from the carrier gas discharged from the impulse furnace 10 in a state wherein no sample is put into the heated graphite crucible 11. Next, the control unit 170 maintains the forth state, initiates the analysis by the quadrupole mass spectrometer 40 at a time when a predetermined time passes after the sample is put into the graphite crucible 11, the analysis by the quadrupole mass spectrometer 40 is initiated, and the control unit 170 obtains a measurement analysis data (date shown by a solid line in FIG. 6) indicating a chronological change of the current intensity obtained by the mixed gas comprising the carrier gas and the sample gas discharged from the heated impulse furnace 10 with the sample put in the graphite crucible 11. Then, similar to the above-mentioned calibration processes, the information processing unit 42 of the quadrupole mass spectrometer 40 calculates the concentration of Ar contained in the sample based on the reference analysis data and the measurement analysis data. The present claimed inventor found that there is a phenomenon that the reference analysis data that should generally coincide with the measurement analysis data rises out of the measurement analysis data in a later half of the detection time period when the peak of Ar appears (time period indicated by an arrow in FIG. 6) based on the comparison between the reference analysis data and the measurement analysis data as shown by a two-dot chain line in FIG. 6. In case of comparing the reference calibration data with the measurement calibration data, the reference calibration data generally coincides with the measurement calibration data during a time period before and after the detection time period (time period indicated by an arrow in FIG. 4) when the peak of Ar appears. Then, the inventor found this phenomenon occurring on the reference analysis data and the measurement analysis data obtained by this ordinary analysis operation is one of the factors of deterioration in the measurement accuracy.

In order to improve deterioration in the measurement accuracy due to this phenomenon, as a result of the repeated trial and error by the inventor, a fact was found that the phenomenon can be restrained by putting a bath agent (a bath agent containing Fe as being the main component of the sample in this embodiment) containing an element as being a main component of the sample gas into the graphite crucible 11 in case of conducting degassing during each process of the analysis.

Figure 7:
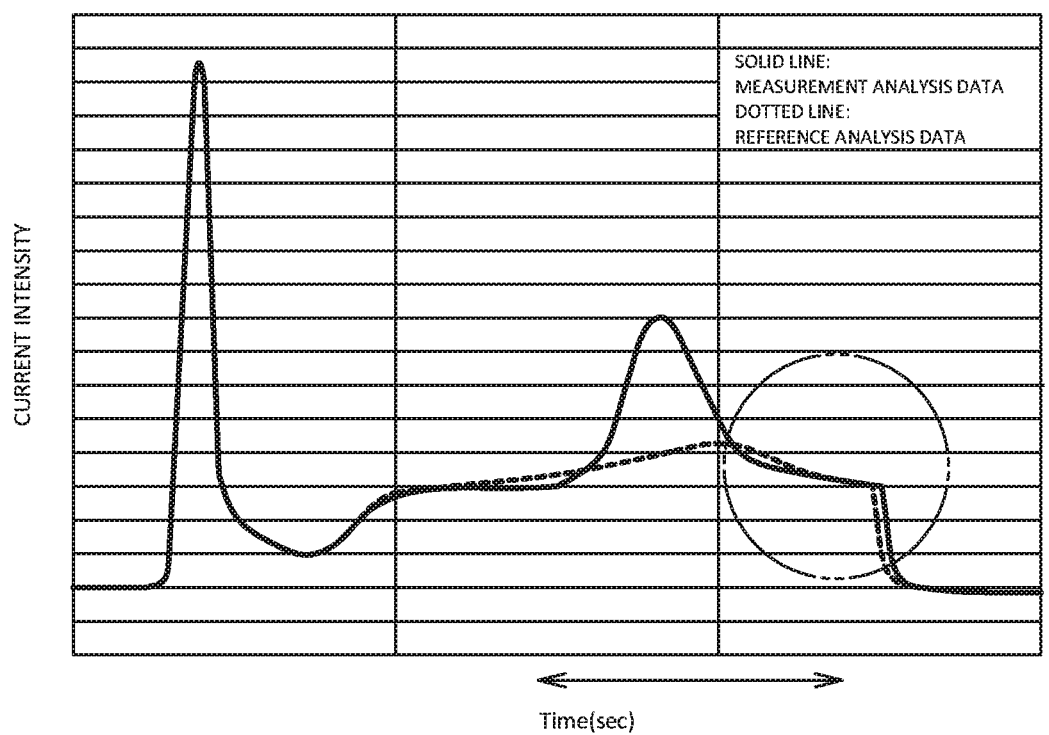
FIG. 7 is a graph showing the reference analysis data and the measurement analysis data obtained by an improved analysis operation of the element analysis device in accordance with this embodiment.

More specifically, in the improved analysis operation, first the control unit 170 sets the element analysis device 100 in the third state, conducts degassing by applying the electric currents to the graphite crucible 11 while supplying the carrier gas to the impulse furnace 10 from the carrier gas supplier 20 with keeping the third state, further conducts degassing by applying the electric currents to the graphite crucible 11 into which the bath agent is put, switch the third state to the forth state with keeping the state wherein the electric currents are applied, initiates the analysis by the quadrupole mass spectrometer 40 at a time when a predetermined time passes after switching to the forth state, and obtains the reference analysis data (data indicated by a dotted line in FIG. 7) indicating the chronological change of the current intensity obtained by the carrier gas discharged from the heated impulse furnace 10 in a state that the bath agent is put into the graphite crucible 11. Next, the control unit 170 keeps the forth state, initiates the analysis by the quadrupole mass spectrometer 40 at a time when a predetermined time passes after the sample is put into the graphite crucible 1, and obtains the measurement analysis data (data indicated by a solid line in FIG. 7) indicating the chronological change of the current intensity obtained by the mixed gas comprising the carrier gas and the sample gas discharged from the heated impulse furnace 10 in a state that the sample is put into the graphite crucible 11. Then, as shown by a two-dot chain line in FIG. 7, the reference analysis data generally coincides with the measurement analysis data in a later half of the detection time period when the peak of Ar appears, and there is no above-mentioned phenomenon. As a result of this, it is possible to improve the accuracy of the concentration of Ar contained in the sample gas calculated by the information processing unit 42 of the quadrupole mass spectrometer 40 based on the reference analysis data and the measurement analysis data by the same calculation method as the calibration method. For the reference analysis data and the measurement analysis data, in case that the time period wherein the current intensity of the reference analysis data is lower than the current intensity of the measurement analysis data and the time period wherein the current intensity of the reference analysis data exceeds the current intensity of the measurement analysis data exist together in the above-mentioned detection time period, a difference area calculated based on the plot points measured in the time period wherein the current intensity of the reference analysis data is lower than the current intensity of the measurement analysis data is set positive, and a difference area calculated based on the plot points measured in the time period wherein the current intensity of the reference analysis data exceeds the current intensity of the measurement analysis data is set negative, and the concentration of Ar contained in the measurement calibration gas is calculated based on the number value obtained by summing up both of the difference areas. In this case, as shown in FIG. 7, in the time period wherein the current intensity of the reference analysis data exceeds the current intensity of the measurement analysis data, if there is no big difference between the current intensity of the reference analysis data and the current intensity of the measurement analysis data, the concentration of Ar contained in the measurement calibration gas may be calculated based on the difference area calculated based on the plot points measured in the time period wherein the current intensity of the reference analysis data is lower than the current intensity of the measurement analysis data while ignoring the difference area calculated based on the plot points measured in the time period wherein the current intensity of the reference analysis data exceeds the current intensity of the measurement analysis data.

Following operations are conducted concretely as an improved analysis operation. More specifically, first, the control unit 170 sets the element analysis device 100 in the third state, with this state kept, $W_1$ kw of the electric power is continuously applied to the graphite crucible 11 for a predetermined period $t_1$, and then $W_2$ kw of the electric power is applied to the graphite crucible 11 for a predetermined time period $t_2$. Then, degassing is initiated after $W_1$ kw of the electric power is first applied, the bath agent containing X g of Fe is put into the graphite crucible 11 and degassing is initiated at a time when a predetermined time period $t_3$ passes after $W_1$ kw of the electric power is first applied, the control unit 170 switches the element analysis device 100 from the third state to the forth state in a state of keeping $W_2$ kw of the electric power being applied to the graphite crucible 11, and the reference analysis data is obtained by measuring the chronological change of the electric power intensity by the use of the quadrupole mass spectrometer 40 at a time when a predetermined time period $t_5$ passes after the element analysis device 100 is switched to the forth state. Next, the control unit 170 keeps the element analysis device 100 in the forth state, keeps the state wherein $W_2$ kw of the electric power is continuously applied to the graphite crucible 11 for the predetermined time period $t_5$ in succession, the Ar containing sample Y g is put into the graphite crucible 11 at a time when a predetermined time period $t_6$ passes after $W_2$ kw of the electric power is applied, and the measurement analysis data is obtained by measuring the chronological change of the electric power intensity by the use of the quadrupole mass spectrometer 40 at a time when a predetermined time period $t_7$ passes. The predetermined time period $t_1 \sim t_7$, and $W_1 \sim W_2$ are appropriately determined.

Other Embodiment

Figure 8:
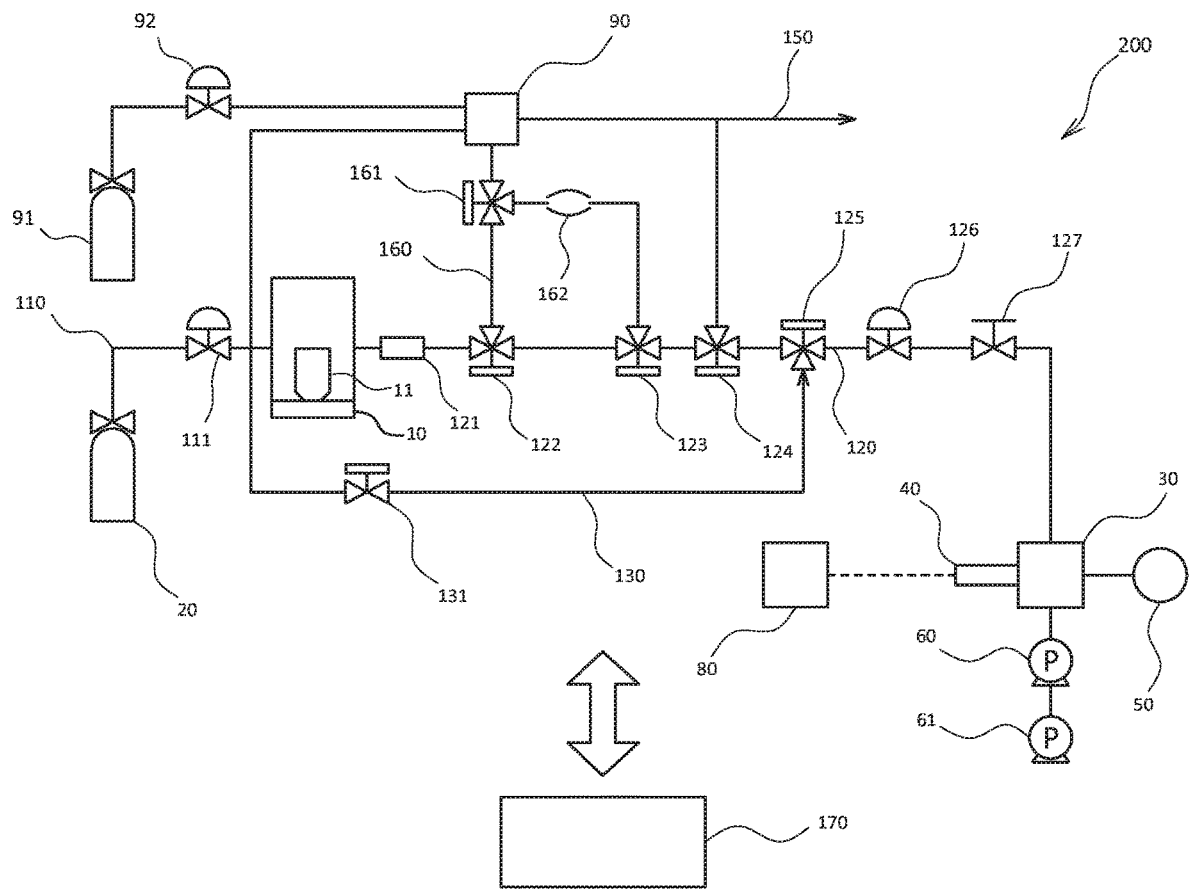
FIG. 8 is a pattern view showing an element analysis device in accordance with other embodiment.

An element analysis device 200 in accordance with other embodiment is, as shown in FIG. 8, a modification of the element analysis device 100 in accordance with the above-mentioned embodiment, and concretely is the same structure as that of the element analysis device 100 except that the branch line 140, the suction pump 141 and the leak valve 70 of the element analysis device 100 are removed. In accordance with this arrangement, it is possible to introduce all amount of the mixed gas discharged from the heating furnace 10 into the vacuum chamber 30.

In the above-mentioned embodiment, the steel material that contains Ar is used as the sample, however, a metal such as titanium, iron, tin or tungsten, or a metal material such as an iron ore material whose main component is the metal or a super alloy may be the sample.

In addition, in the above-mentioned embodiment. Ar contained in the sample is the object to be measured, however, for example, other element, concretely oxygen, nitrogen, hydrogen or sulfur, contained in the sample gas produced by vaporizing a metal sample may be the object to be measured. In case that the object to be measured is oxygen, nitrogen or hydrogen, a quantitative analysis is conducted on oxygen by the use of an analysis device from $CO_2$ obtained by converting CO contained in the mixed gas discharged from the heating furnace in an oxidizing part, the quantitative analysis is conducted on hydrogen by the use of an analysis device from $H_2O$ obtained by converting $H_2$ contained in the mixed gas in an oxidizing part, and the quantitative analysis is conducted on nitrogen by the use of an analysis device from $N_2$. In case of conducting the quantitative analysis on oxygen by the use of the analysis device from the above-mentioned $CO_2$, if the quantitative analysis is not conducted on $N_2$, the quantitative analysis may be conducted by the analysis device on CO contained in the mixed gas after removing $N_2$ by the use of a nitrogen removing agent. In addition, a mass spectrometer, an NDIR or a TCD may be used as the analysis device used for conducting the quantitative analysis, however, in case that a mass spectrometer for conducting the quantitative analysis by extracting the element in vacuum atmosphere is used as the mass spectrometer, it is preferable to arrange the mass spectrometer in a downstream side from the second pressure regulator, more preferably in a downstream side from a branch point between the discharging line 120 and the branch line 140. In addition, in case of using the NDI or the TCD, the NDI or the TCD may be arranged in the downstream side from the dust filter 121. The oxidizing part may comprise copper oxide, and the de-carbon dioxide part may comprise a reagent impregnating Ascarite, silica gel with potassium hydroxide or sodium hydroxide.

Figure 9:
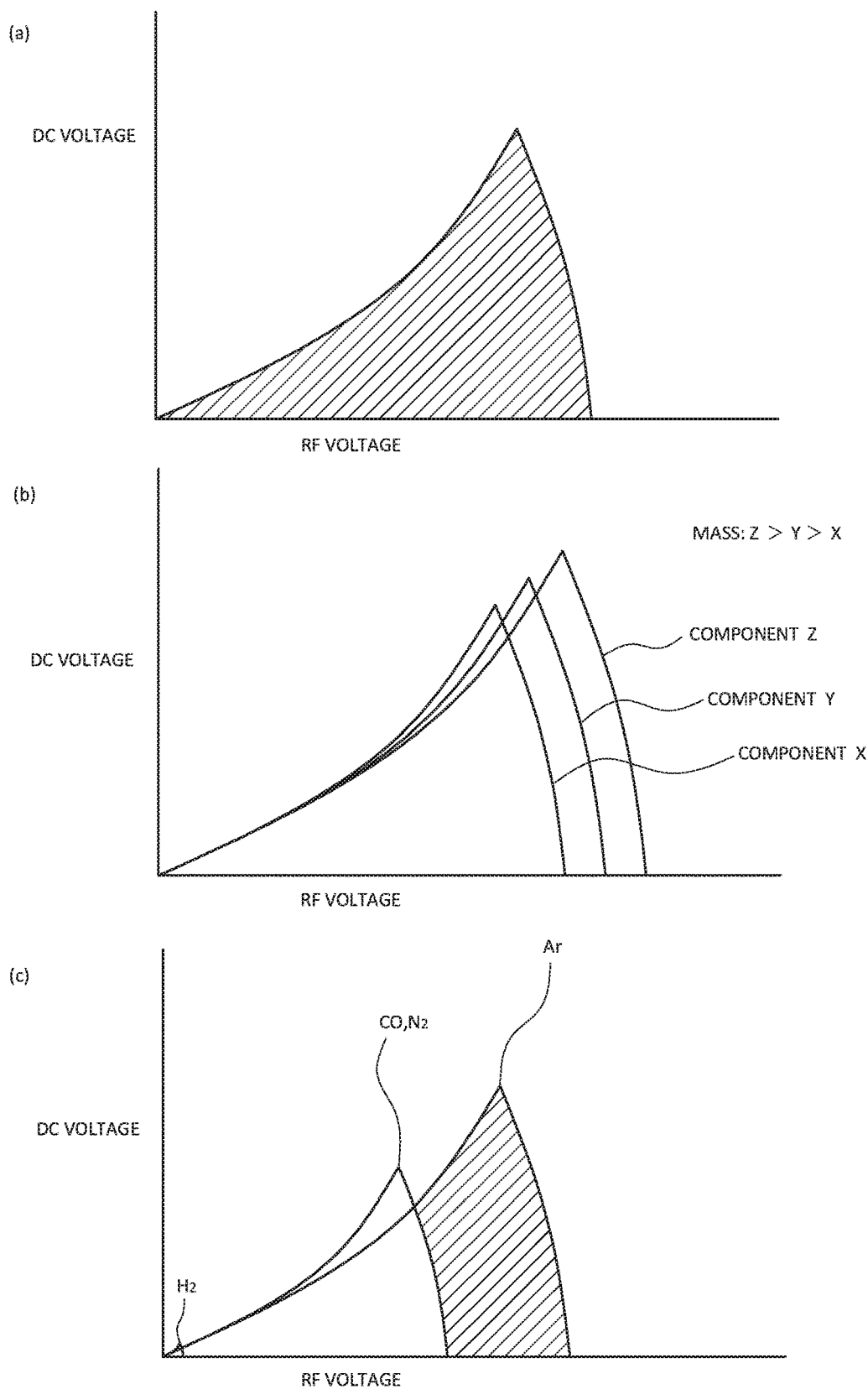
FIG. 9 is a graph to explain a relationship among a DC voltage, a RF voltage and a stable range in a quadrupole mass spectrometer.

A peak waveform of the data indicating the chronological change of the current intensity obtained by the quadrupole mass spectrometer 40 changes in accordance with DC voltage and RF voltage applied to the quadrupole part. More specifically, a range of the DC voltage and RF voltage (hereinafter called as "a stable range") that can pass the quadrupole part for each component (more precisely, a mass to charge ratio decided for each component m/z: m indicates a mass, z indicates a charge, and z/m is a value that depends on the mass) of the sample gas is decided for the quadrupole mass spectrometer 40, and for example, the stable range of a predetermined component shows a chevron indicated by a solid hatching in FIG. 9(*a*) in case that the DC voltages are plotted on a vertical axis and the RF voltages are plotted on a horizontal axis. If the DC voltage and the RF voltage that fall within the stable range are selected, the predetermined component passes the quadrupole part so that the predetermined component can be detected. However, if the DC voltage and the RF voltage that fall out of the stable range are selected, the predetermined component cannot pass the quadrupole part so that the predetermined component cannot be detected. Then, the peak waveform forms a gentle incline while the DC voltage is low in the stable range, and the peak waveform forms a steep incline while the DC voltage is high in the stable range. The stable range differs for each component, and as shown in FIG. 9(*b*), the more the mass of the component increases, the bigger the chevron shape becomes and the peak of the chevron shape is shifted to a higher RF voltage. Then, if the mass of the component is close to each other like the component X, Y, Z, each of the stable ranges X, Y and Z overlaps. As a result of this, in case that the component Y of the sample gas that contains the components X, Y and Z shown in FIG. 9(*b*) is the object to be measured, if the DC voltage is decreased in the stable range Y in order to improve the measurement accuracy and the DC voltage in the stable range X, Z is selected, not only the component Y but also the components X and Z also pass the quadrupole part so that it is not possible to detect the component Y alone. Generally since the sample gas contains not only the component as the object to be measured but also other component, conventionally the measurement was conducted by increasing the DC voltage within the stable range as much as possible to avoid the situation and by selecting the DC voltage locating in the vicinity of the peak in the stable range.

However, if each mass of the component contained in the mixed gas evaporated by heating the material sample containing Ar is compared, the mass of CO is 28, the mass of $N_2$ is 28, the mass of $H_2$ is 2 and the mass of Ar is 40 so that there is some difference between the mass of Ar and the mass of other components. Then, as shown in FIG. 9(*c*), even though the DC voltage is decreased in a part (for example, a part indicated by solid hatchings in FIG. 9(*c*)) that is in the stable range of Ar and that does not overlap with the stable range of other element, it is possible to conduct the measurement without detecting other component so that the peak waveform drawing a gentle incline can be obtained as a data indicating the chronological change of the current intensity, resulting in improvement of the measurement accuracy. If an oxidation part is provided and the component whose mass is similar to that of Ar such as $CO_2$ (the mass: 44) is contained in the sample gas, the measurement can be conducted by selecting the DC voltage in the vicinity of the peak in the stable range. In addition, in case that there is some difference in the mass of each component contained in the sample gas, it is also possible to conduct the measurement with decreasing the DC voltage similar to the above-mentioned.

Figure 10:
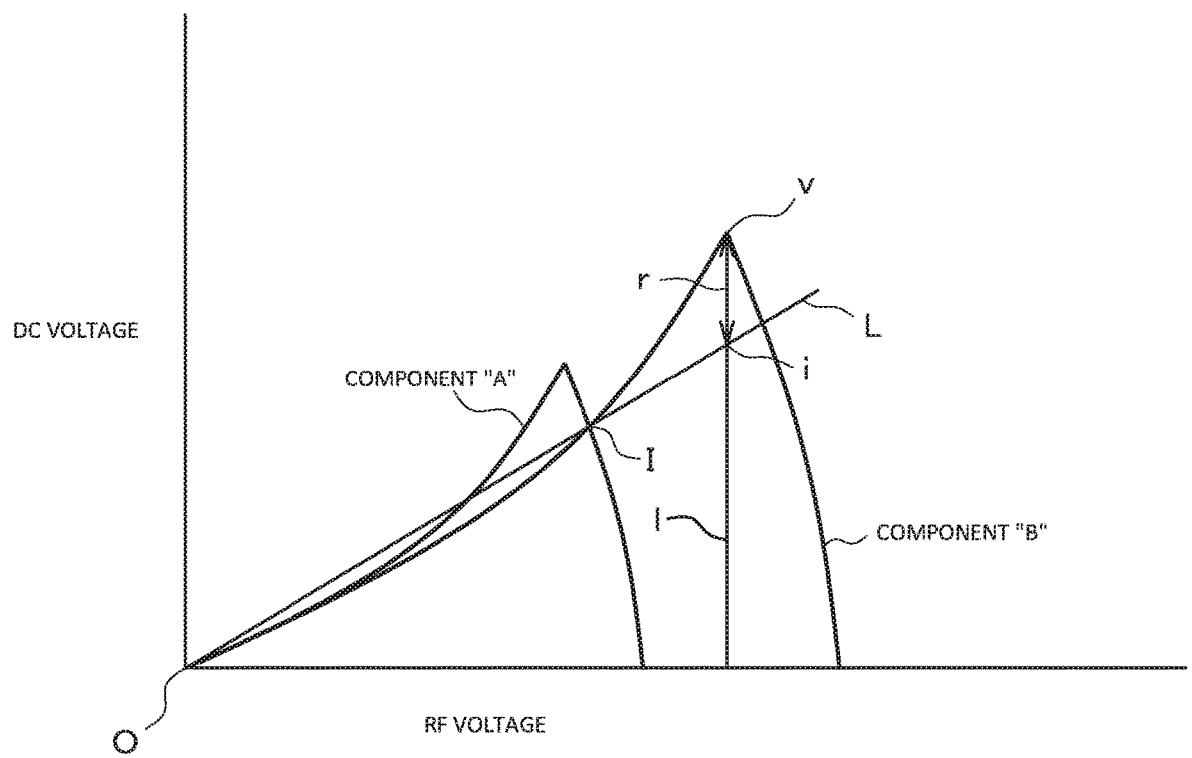
FIG. 10 is a graph to explain a relationship among a DC voltage, a RF voltage and a stable range in the quadrupole mass spectrometer.

Then, in case of conducting the measurement on the mixed gas that contains a plurality of components as being the object to be measured, it is possible to determine the RF voltage/the DC voltage (hereinafter also called as the RF/DC ratio) at a time of measurement by the following procedure. If explained based on FIG. 10, first, two components whose difference between the mass numbers of the components adjacent to each other is the smallest are picked up among a plurality of the components as being the object to be measured. Next, specify an intersection "I" between an outline of a component (hereinafter also called as a component "A") whose mass number is small in the stable range and an outline of a component (hereinafter also called as a component "B") whose mass number is bigger in the stable range in a graph wherein the RF voltages are plotted on a horizontal axis and the DC voltages are plotted on a vertical axis. The intersection "I" is an intersection between a part where the DC voltage decreases as the RF voltage increases in the stable range of the component (A) and a part where the DC voltage increases as the RF voltage increases in the stable range of the component (B). Next, draw a straight line (L) connecting the origin (O) where the DC voltage and the RF voltage become 0 and the intersection "I". Next, obtain an intersection "i" between a perpendicular line "l" drawn on the RF voltage axis from a vertex "v" of the component "B" in the stable range and the straight line "L". A value of the RF voltage/the DC voltage in the range "r" between the vertex "v" (peak) and the intersection "i" becomes the RF/DC ratio that can be employed at a time of measurement.

In case that the component "A" is $H_2O$ with mass number 18 and the component "B" is Ar with mass number 44, more specifically, in case that a difference of the mass number between the component "A" and the component "B" is 22, the intersection "I", the vertex "v" and the intersection "i" are as follows.

Intersection "I": RF voltage, DC voltage=0.17, 0.58
Vertex "v": RF voltage, DC voltage=0.706, 0.23699
Intersection "i" RF voltage, DC voltage=0.706, 0.2017
Then, the RF/DC ratio on the vertex "v" becomes 5.958 and the RF/DC ratio on the intersection "i" becomes 7.000. As a result of this, it is possible to select the RF voltage and the DC voltage so as to make the RF/DC ratio 5.958~7.0000 and to conduct the measurement. In this case, the closer the RF/DC ratio approaches, the more the measurement accuracy improves at a time of the measurement.

More specifically, in case of measuring the mixed gas containing a plurality of components by the quadrupole mass spectrometer, the RF/Dc ratio may be selected by the use of a method for selecting the RF/DC ratio. In a graph with the RF voltage plotted on a horizontal axis and the DC voltage plotted on a vertical axis indicating the stable range of two adjacent components wherein the difference of the mass numbers thereof is the smallest among a plurality of components, and the straight line "L", the perpendicular line "I" and the second intersection (intersection "i") are obtained and the RF/DC ratio is selected in the range "r" between the RF/DC ratio in the vertex "v" and the RF/DC ratio in the second intersection "i" by using the first intersection (intersection "I") as being the intersection of the two visible outlines of the two components in the stable range, the straight line "L" extending from the origin "O" where both the RF voltage and the DC voltage become 0 to pass the first intersection "I", the second intersection "i" of the straight line "L" and the perpendicular line "1" drawing from the vertex "v" down to the RF voltage axis, and the vertex "v" where the DC voltage is the highest in the stable range of the component whose mass is bigger.

In addition, in the above-mentioned embodiment, the quantitative analysis is conducted on the reference analysis data and the measurement analysis data obtained by the sensor part 41 of the quadrupole mass spectrometer 40 by the information processing unit 42, the quantitative analysis may be conducted based on the reference analysis data and the measurement analysis data by an information processing unit provided separately from the quadrupole mass spectrometer 40.

In addition, the heating furnace is used in the above-mentioned embodiment, however, a high frequency furnace using a porcelain crucible may be used.

In addition, the vacuum chamber 30 and the turbo suction pump 6 are connected through the connecting pipe 35 whose flow channel has a shape of extending to the downstream side in the above-mentioned embodiment, however, a flow channel having the same shape as that of the above-mentioned embodiment may be integrally formed at a connecting between the vacuum chamber 30 and the turbo suction pump 6.

In addition, for the element analysis device 100 using the quadrupole mass spectrometer 40, as a connection mode of each component to the vacuum chamber 30 (hereinafter also called as "chamber"), like disclosed in, for example, Japanese Unexamined Patent Application Publication No. 2008-47597, the discharging line and the quadrupole mass spectrometer are connected to face each other with the chamber, an introducing port is arranged along an inner surface of the chamber 30 as a distal end of a discharging line, an intake port of the quadrupole mass spectrometer 40 is provided along the inner surface of the chamber 30 to face the introducing port, and a suction pump is connected to the chamber 30 so as to be orthogonal to an opening direction the introducing port and the intake port. However, in accordance with the connection mode of each component to the vacuum chamber 30, a distance between the introducing port and the intake port becomes long so that almost all of the sample gas introducing from the introducing port to inside of the chamber 30 is discharged into outside of the chamber 30 from the suction pump. As a result of this, the amount of the sample gas taken into the quadrupole mass spectrometer from the intake port becomes small, resulting in a factor of lowering the analysis accuracy.

Then, in order to improve the analysis accuracy of the quadrupole mass spectrometer 40, following modes of connecting each component to the chamber 30 may be adopted.

More specifically, for the element analysis device, the chamber to which the quadrupole mass spectrometer is connected, and the sample gas introduced into the internal space of the chamber through the introducing port is taken into the quadrupole mass spectrometer through the intake port that opens into the internal space of the chamber, the introducing port and the intake port open to face each other with an interval formed therebetween, and either one of them or both of them are arranged in the inside of the chamber.

In accordance with this arrangement, it is possible to make the introducing port and the intake port close in the chamber so that the sample gas discharged into the chamber through the introducing port is taken into the quadrupole mass spectrometer through the intake port efficiently, resulting in improvement of the analysis accuracy of the quadrupole mass spectrometer.

In addition, the element analysis device may also adopt the following configuration. More specifically, the element analysis device may further comprise a discharging mechanism that discharges the sample gas introduced into the inside space of the chamber through the introducing port to outside of the chamber, and the intake port may be arranged to be shifted to the discharging direction side of the discharging mechanism relative to the introducing port. In accordance with this arrangement, the sample gas whose traveling direction is changed due to being sucked by the discharging mechanism after being introduced into the chamber through the introducing port is headed for the intake port. Then an amount of the sample gas taken from the intake port further increases so that the analysis accuracy of the quadrupole mass spectrometer is improved much more.

In addition, the above-mentioned element analysis device may have an arrangement wherein the opening direction of the intake port and the opening direction of the introducing port face mutually opposed directions. In addition, the discharging direction of the discharging mechanism may be orthogonal to either one of or both of the opening direction of the intake port and the opening direction of the introducing port. In addition, the intake port may be arranged at a distal end of the quadrupole mass spectrometer to be connected to the chamber. In addition, the introducing port may be arranged at a distal end of the pipe member to be connected to the chamber. The pipe member is a component of the introducing line constituting a distal end to be connected to the chamber.

In addition, the introducing port may be so configured that a position of the introducing port to the chamber can be adjusted by fitting of a screw groove arranged on an outer peripheral surface of the pipe member into a screw groove arranged on an inner peripheral surface of the connection port of the chamber to which the pipe member is connected. In accordance with this arrangement, it is possible to adjust the position of the introducing port to the chamber easily.

In addition, the ionization part that ionizes the sample gas as being the component element of the quadrupole mass spectrometer may be provided inside of the intake port, and the sample gas may be introduced from the introducing part into the ionization part toward a position opposite to the discharging direction of the discharging mechanism. In accordance with this arrangement, it is possible to efficiently pass the sample gas introduced from the introducing port through the ionization part, resulting in further improvement of the analysis accuracy of the quadrupole mass spectrometer.

An embodiment of connection mode of the discharging line, the quadrupole mass spectrometer and the suction pump to the chamber will be explained with reference to drawings.

Figure 11:
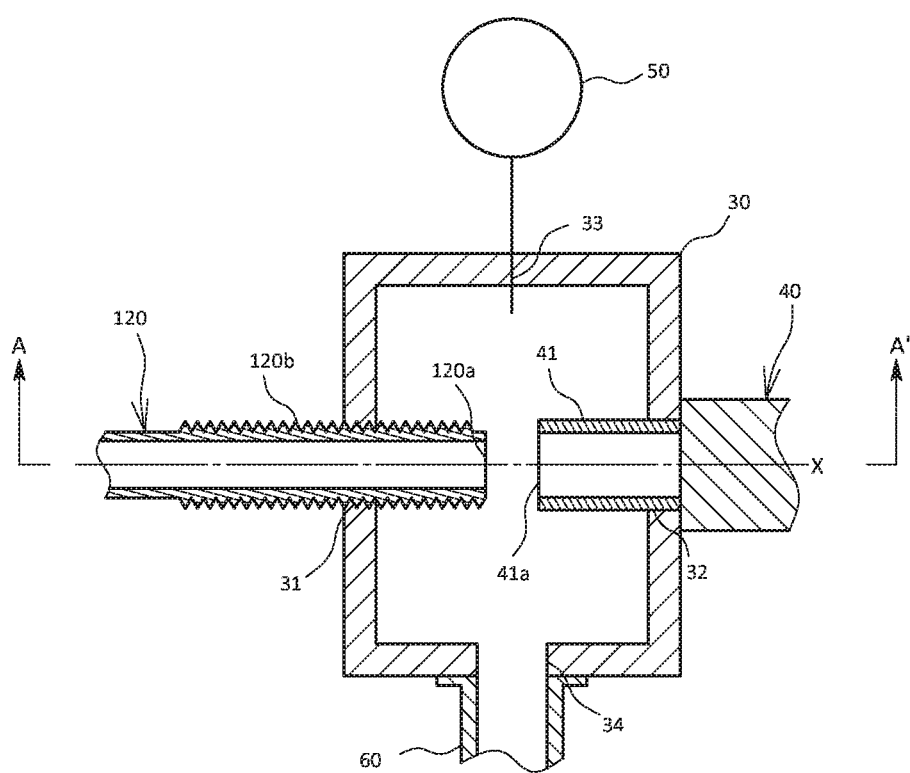
FIG. 11 is a cross-sectional view showing a connection mode of a chamber of the element analysis device in accordance with other embodiment.
Figure 12:
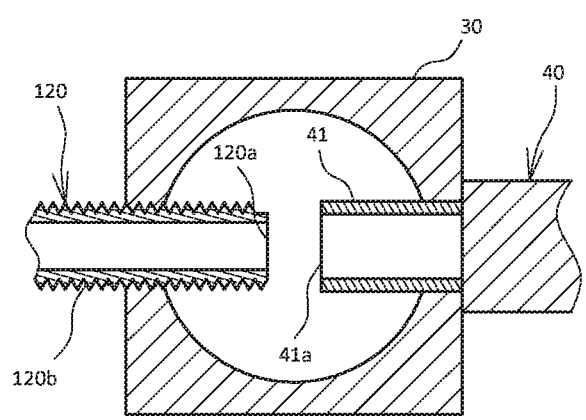
FIG. 12 is a cross-sectional view showing a connection mode of a chamber of the element analysis device in accordance with a further different embodiment.

An embodiment of the connection mode is, as shown in FIG. 11 and FIG. 12, a chamber 30 whose appearance is rectangular parallelepiped having a cylinder internal space, and connection ports 31, 32, 33, 34 are provided for each of two mutually facing side surfaces and an upper and a lower surfaces respectively. The chamber 30 has an arrangement that the discharging line 120 and the quadrupole mass spectrometer 40 are connected to the connection port 31 of one side surface and the connection port 32 of the other side surface respectively, and the pressure sensor 50 and an exhaust pump 60 are connected to the connection port 33 of the upper surface and the connection port 34 of the lower surface respectively. The exhaust pump 60 that is bigger and heavier than the pressure sensor 50 is preferably connected to the connection port 34 of the lower surface of the chamber 30.

The discharging line 120 is so arranged that a connecting part 120b comprising a pipe member is inserted into the connection port 31 of the chamber 30 and an introducing port 120a that opens toward the quadrupole mass spectrometer 40 is arranged at a distal end of the connecting part 120b. In addition, the quadrupole mass spectrometer 40 is so arranged that a sensor part 41 is inserted into the connection port 32 of the chamber 30 and an intake port 41a that opens toward the discharging line 120 is arranged at a distal end of the sensor part 41. Both the introducing port 120a and the intake port 41a are positioned concentrically to the axial line (X) penetrating two side surfaces facing each other, and open toward mutually opposed directions at intervals. In addition, both of the introducing port 120a and intake port 41a are arranged in the inside of the chamber 30.

In addition, the discharging line 120 is connected and fixed to the chamber 30 with a screw groove arranged on an outer surface of the connecting part 120b screwed to a screw groove arranged on an inner surface of the connection port 31. With this arrangement, it is possible to move the introducing port 120a along the axial line (X) by rotating the connecting part 120b relative to the connection port 31 so that a distance between the discharging line 120 and the intake port 41a can be freely adjusted.

In accordance with this arrangement, since the distance between the introducing port 120a and the intake port 41a can be reduced, the sample gas discharged into the internal space of the chamber 30 through the introducing port 120a reaches the intake port 41a more before the sample gas is discharged from the internal space of the chamber 30 by the exhaust pump 60. As a result of this, the amount of the sample gas taken into the quadrupole mass spectrometer 40 through the intake port 41a increases, resulting in improvement of the analysis accuracy of the quadrupole mass spectrometer 40.

Figure 13:
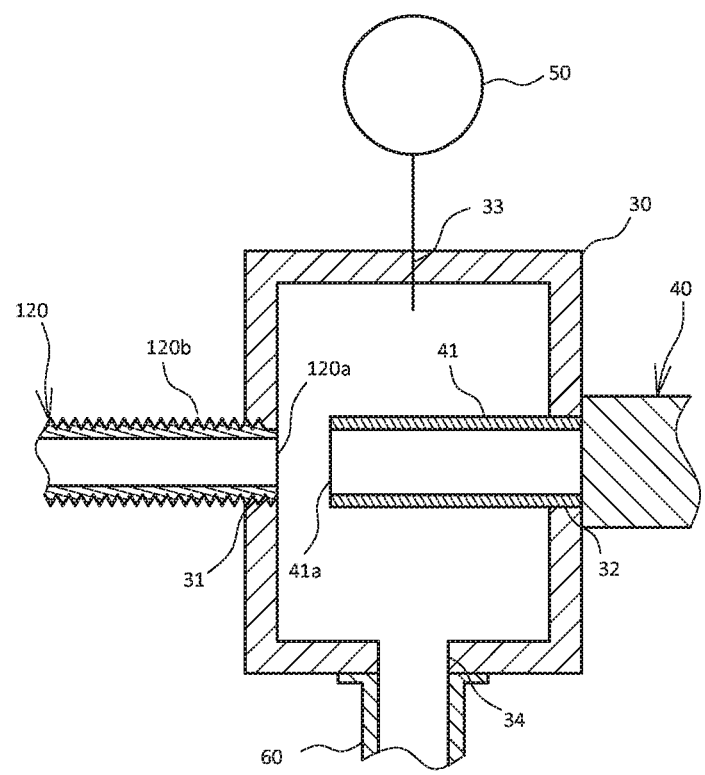
FIG. 13 is a cross-sectional view showing a connection mode of a chamber of the element analysis device in accordance with a further different embodiment.
Figure 14:
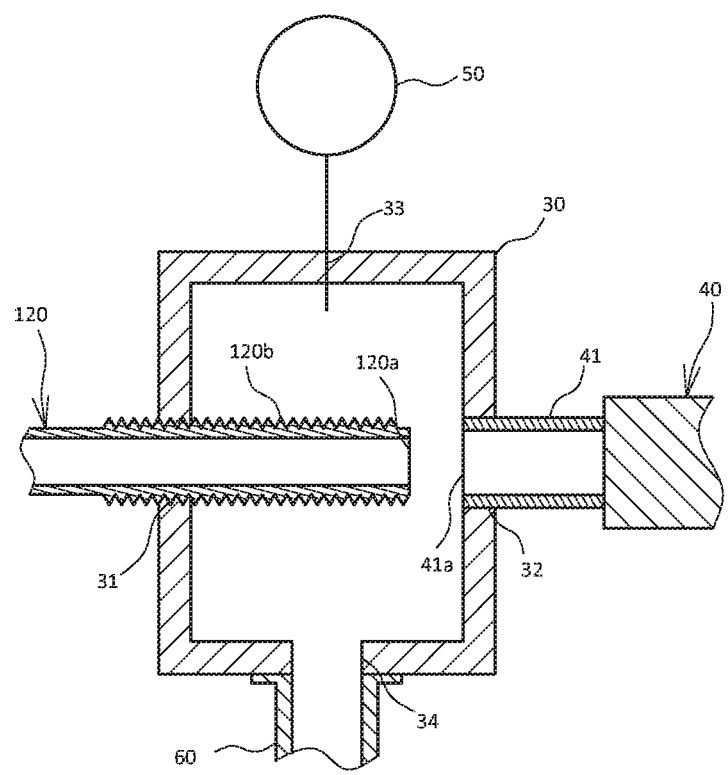
FIG. 14 is a cross-sectional view showing a connection mode of a chamber of the element analysis device in accordance with a further different embodiment.
Figure 15:
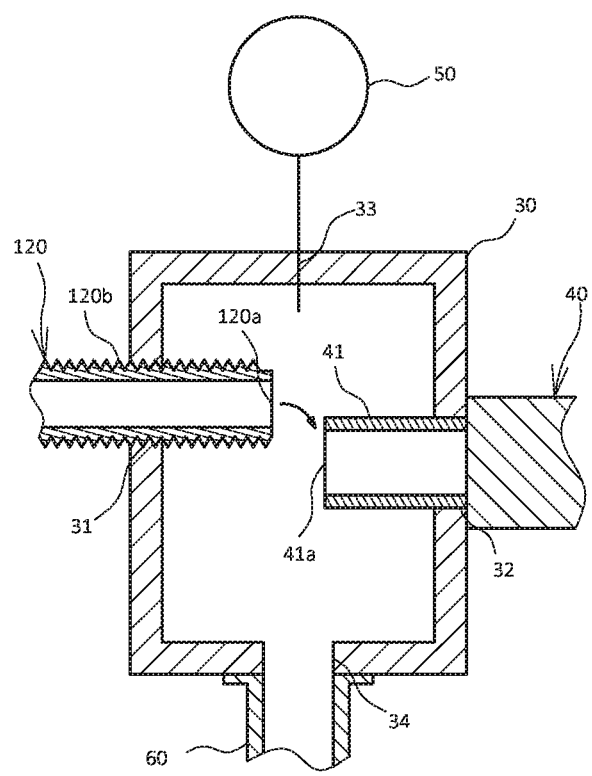
FIG. 15 is a cross-sectional view showing a connection mode of a chamber of the element analysis device in accordance with a further different embodiment.

As a modified embodiment of the connection mode represented is embodiments shown in FIG. 13~FIG. 15. The embodiment shown in FIG. 13 is so arranged that an opening end of the introducing port 120a is positioned to be flat to an inner surface of the chamber 30, and the intake port 41a of the quadrupole mass spectrometer 40 is positioned inside of the chamber 30 in the vicinity of the introducing port 120a. In addition, the embodiment shown in FIG. 14 is so arranged that an opening end of the intake port 41a of the quadrupole mass spectrometer 40 is positioned to be flat to the inner surface of the chamber 30, and the introducing port 120a is positioned inside of the chamber 30 in the vicinity of the intake port 41a. In accordance with these embodiments, a gap between the introducing port 120a and the intake port 41a is positioned in a deviated position from just above the connection port 34 to which the exhaust pump 60 is connected. As a result of this, since the sample gas from the introducing port 120a to the intake port 41a is difficult to be influenced by the suction of the exhaust pump 60, the amount of the sample gas taken into the quadrupole mass spectrometer 40 increases, resulting in improvement of the analysis accuracy of the quadrupole mass spectrometer 40.

The embodiment shown in FIG. 15 is so arranged that the introducing port 120a is positioned in a deviated position from the intake port 41a of the quadrupole mass spectrometer 40 toward an opposite direction to the exhaust direction by the exhaust pump 60. In accordance with this embodiment, the sample gas discharged from the introducing port 120a is taken in the intake port 41a during a process of being sucked by the exhaust pump 60. As a result of this, the amount of the sample gas taken into the quadrupole mass spectrometer 40 increases, resulting in the improvement of the analysis accuracy of the quadrupole mass spectrometer 40.

In each of the above-mentioned embodiments, the intake port 41a is arranged for the sensor part 41 of the quadrupole mass spectrometer 40, however, it is not limited to this. As the other embodiment of the connection mode, the sample gas may be taken into the sensor part 41 through a pipe mounted on the sensor part 41a of the quadrupole mass spectrometer 40. In this case, the intake port 41a arranged at a distal end of the pipe may be positioned near the introducing port 120a. In addition, a pipe may be placed between the connection port 31 and the connection port 32 arranged on the opposing side surfaces of the chamber 30, a slit may be provided in the middle of the pipe, and the sample gas that leaks from the slit may be discharged by the use of the exhaust pump 60. In this case, one side becomes the introducing port 120a and the other side becomes the intake port 41a across the slit of the pipe.

Furthermore, as the other embodiment of the connection mode, the introducing port 120a may introduce the sample gas toward the ionization part 43 that is arranged inside of the intake port 41a and as being the component element of the quadrupole mass spectrometer 40 to ionize the sample gas, or toward a position opposite to the discharging direction of the exhaust pump 60.

An element analysis system that adopts either one of the connection mode of the chamber 30 comprises a heating furnace that produces a sample gas by heating a crucible that contains a sample while introducing a carrier gas and by evaporating at least a part of the sample gas, a chamber that introduces a mixed gas comprising the carrier gas and the sample gas discharged from the heating furnace into an internal space of the chamber through an introducing port, and a quadrupole mass spectrometer that is connected to the chamber and that takes the sample gas contained in the mixed gas from an intake port that opens to the internal space of the chamber. In addition, the introducing port and the intake are arranged to open to face each other to leave spaces therebetween and either one of the introducing port and the intake port or both of them are arranged inside of the chamber. More concretely, the element analysis device further comprises a first pressure regulator that controls pressure of the carrier gas introduced into the heating furnace, and a second pressure regulator that controls pressure of the mixed gas introduced into the mass spectrometer.

INDUSTRIAL APPLICABILITY

An element analysis device wherein a heating furnace and a mass spectrometer such as a quadrupole mass spectrometer that conducts a quantitative analysis on an element in a vacuum atmosphere are combined conducts the quantitative analysis on the element contained in a sample gas with high accuracy.

The invention claimed is:
1. An element analysis device comprising
a heating furnace that produces a sample gas by heating a crucible that contains a sample while introducing a carrier gas so as to evaporate at least a part of the sample,
a mass spectrometer that extracts an element contained in the sample gas in a mixed gas comprising the carrier gas and the sample gas discharged from the heating furnace in a vacuum atmosphere and that conducts a quantitative analysis on the element,
a first pressure regulator that controls pressure of the carrier gas to be introduced into the heating furnace, and
a second pressure regulator that controls pressure of the mixed gas to be introduced into the mass spectrometer.

2. The element analysis device according to claim 1, further comprising
a vacuum chamber to which the mass spectrometer is connected, wherein
total amount of the mixed gas discharged from the second pressure regulator is introduced into the vacuum chamber.

3. The element analysis device according to claim 1, further comprising
a suction pump that is arranged on a branch line that branches and extends from a position between the second pressure regulator and the mass spectrometer and that sucks the mixed gas whose pressure is controlled by the second pressure regulator.

4. The element analysis device according to claim 1, wherein
the pressure of the carrier gas to be introduced into the heating furnace is controlled by the first pressure regulator within a range more than or equal to 20 kPa and less than or equal to 80 kPa.

5. The element analysis device according to claim 1, wherein
the sample is an Ar containing sample.

6. The element analysis device according to claim 1, wherein
the mass spectrometer is a quadrupole mass spectrometer, and comprising
an information processing unit that conducts a quantitative analysis on the element contained in the sample gas based on
a reference analysis data that indicates a chronological change of current intensity obtained (i) by heating the crucible into which a bath agent containing a main component of the sample is put while introducing the carrier gas into the heating furnace, (ii) by heating the crucible without putting the sample into the crucible while introducing the carrier gas into the heating furnace and (iii) by introducing the carrier gas discharged from the heating furnace into the quadrupole mass spectrometer, and
a measurement analysis data that indicates the chronological change of the current intensity obtained (i) by putting the sample into the crucible and heating the crucible while introducing the carrier gas into the heating furnace, and (ii) by introducing the mixed gas comprising the carrier gas and the sample gas discharged from the heating furnace into the quadrupole mass spectrometer.

7. The element analysis device according to claim 1, wherein the second pressure regulator is provided on a discharging line which guides the mixed gas discharged from the heating furnace to the mass spectrometer.

8. The element analysis device according to claim 1, further comprising a flow rate adjuster that limits a flow rate of the mixed gas, the flow rate adjuster being arranged in series with the second pressure regulator.

9. An element analysis method for conducting a quantitative analysis on an element contained in a sample gas produced by evaporating a sample, comprising
heating a crucible in a heating furnace into which a bath agent containing a main component of the sample is put while introducing a carrier gas whose pressure is within a range more than or equal to 20 kPa and less than or equal to 80 kPa into the heating furnace,
producing the sample gas by heating the crucible into which an Ar containing sample is put while introducing the carrier gas into the heating furnace,
reducing pressure of a mixed gas comprising the carrier gas and the sample gas discharged from the heating furnace to less than or equal to 1.5 Pa and introducing the decompressed mixed gas into a mass spectrometer, and
extracting the element contained in the sample gas and conducting the quantitative analysis on the element.

10. The element analysis method according to claim 9, comprising
heating the crucible in the heating furnace into which the bath agent containing the main component of the sample is put while introducing the carrier gas whose pressure is within the range more than or equal to 20 kPa and less than or equal to 80 kPa into the heating furnace,
obtaining a reference analysis data that indicates a chronological change of current intensity by heating the crucible in the heating furnace into which no sample is put while introducing the carrier gas into the heating furnace, by reducing the pressure of the carrier gas discharged from the heating furnace to less than or equal to 1.5 Pa and by introducing the decompressed carrier gas into the mass spectrometer, and
obtaining a measurement analysis data that indicates the chronological change of the current intensity by producing the sample gas by heating the crucible in the heating furnace into which the Ar containing sample is put while introducing the carrier gas into the heating furnace, by reducing the pressure of the mixed gas comprising the carrier gas and the sample gas discharged from the heating furnace to less than or equal to 1.5 Pa and by introducing the decompressed mixed gas into the mass spectrometer, and
conducting the quantitative analysis on the element contained in the sample gas based on the reference analysis data and the measurement analysis data.

11. The element analysis method according to claim 9, wherein the mass spectrometer into which the decompressed mixed gas is introduced is a quadrupole mass spectrometer.

* * * * *